United States Patent [19]
Coulson et al.

[11] 3,975,415
[45] Aug. 17, 1976

[54] ORGANOTIN COMPLEXES OF PLATINUM AND PALLADIUM

[75] Inventors: Dale Robert Coulson; Linda P. Seiwell, both of Wilmington, Del.

[73] Assignee: E. I. Du Pont de Nemours and Company, Wilmington, Del.

[22] Filed: May 5, 1975

[21] Appl. No.: 574,352

[52] U.S. Cl. ........................ 260/429 R; 260/429.7; 252/431 P
[51] Int. Cl.² ........................................ C07F 15/00
[58] Field of Search ..................... 260/429 R, 429.7

[56] References Cited
UNITED STATES PATENTS
3,776,929  12/1973  Mrowca ........................ 260/429 R

OTHER PUBLICATIONS

Young, J. Chem. Soc. (1964) p. 5176.

Primary Examiner—Helen M. S. Sneed
Attorney, Agent, or Firm—Anthony P. Mentis

[57] ABSTRACT

Complexes of platinum and palladium contaning organotin ligands are useful as catalysts in dimerizng butadiene. Exemplary in transchloro(triphenoxytin)bis-(triethylphosphine)platinum(II) of the formula $PtCl(P(C_2H_5)_3)_2Sn-(OC_6H_5)_3$.

12 Claims, No Drawings

ORGANOTIN COMPLEXES OF PLATINUM AND PALLADIUM

BACKGROUND OF THE INVENTION

1. Field of the Invention

This invention relates to complexes of platinum and palladium containing organotin ligands and their use as catalysts.

2. Relation to the Prior Art

First row transition element metal complexes which contain organotin ligands, $SnR_3$, where R is alkyl or arylcarboxy or aryloxy are known (U.S. Pat. No. 3,652,507; Bird, et al. J. Chem. Soc. (A), 1971, 1616). Platinum complexes of the type $((C_6H_5)_3P)_2PtCl(SnCl_3)$ have also been prepared (J. F. Young, et al., J. Chem. Soc., 1964, 5176). However, platinum and palladium complexes containing arylcarboxy or aryloxy substituents on tin are unknown.

SUMMARY OF THE INVENTION

This invention concerns trans compounds of the formula $$MX_{2-n}L_2(SnR_3)_n,$$

wherein

M is platinum or palladium;

X is H, Cl, Br or I;

L is $R'_3 P$ or $(R'O)_3P$ in which

R', alike or different, is aryl of 6–12 carbons, alkyl of 1–6 carbons and such groups containing up to two halogens;

R, alike or different, is aryloxy of 6–12 carbons, arylcarboxy of 7–13 carbons and such groups containing up to two halogens; and n is 1 or 2.

"Aryl" means a group derived from a hydrocarbon containing at least one 6-membered aromatic hydrocarbon ring by removal of a hydrogen atom from a ring carbon. Included is phenyl substituted with alkyl groups of 1–6 carbons.

"Alkyl" means a group derived from a saturated aliphatic hydrocarbon by removal of a hydrogen atom.

Preferred L groups include those where R' is alkyl, phenyl and alkyl-substituted phenyl.

Preferred R groups include those where R is phenoxy, phenylcarboxy(benzoyloxy), and such groups substituted with up to two alkyl groups of 1–6 carbons or up to two halogens.

The compounds of the invention are prepared by metathetical reaction as shown in equation (1).

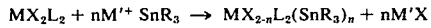

$$MX_2L_2 + nM'^+ SnR_3 \rightarrow MX_{2-n}L_2(SnR_3)_n + nM'X \qquad 1.$$

M' is an alkali metal or tetraaryl or tetraalkylammonium, phosphonium or arsonium cation. Sodium is preferred. In preparing the compounds of the invention by this process, one of the X atoms of $MX_2L_2$ must be Cl, Br or I. The reaction is usually carried out in an ether-type solvent. Examples of such solvents include diethyl ether, diisopropyl ether, di-n-butyl ether, di-n-amyl ether, tetrahydrofuran, dioxane, 2-methoxyethyl ether (diglyme) and 1,2-dimethoxyethane (glyme). A preferred solvent is tetrahydrofuran.

When the product of equation (1) with n=1 is desired, it is preferred to use about 1.0–1.1 moles of $M'^+SnR_3^-$ for each mole of $MX_2L_2$. When the product with n=2 is desired, a larger excess of $M'^+SnR_3^-$ is employed, preferably about 2–5 moles per mole of $MX_2L_2$. With ratios between about 1.1 and 2, mixtures of products may be obtained.

Reaction temperatures employed in the reaction normally range from −20°C. to 75°C. with the preferred temperature range from 10°–35°C. The reaction is conveniently carried out at atmospheric pressure.

SPECIFIC EMBODIMENTS OF THE INVENTION

In the illustrative examples given below all parts are by weight and all temperatures are Centigrade unless otherwise specified.

EXAMPLE 1

To a clear, yellow solution of 5.0263 g of transdichlorobis(triethylphosphine)platinum(II) in 20 ml of tetrahydrofuran (THF) was added a clear, colorless solution of 4.934 g of sodium triphenoxytin monotetrahydrofuranate in 35 ml of tetrahydrofuran. The resulting cloudy, dark yellow solution was stirred for a few minutes at room temperature under nitrogen and then filtered through diatomaceous earth. The filtrate was concentrated under vacuum to about 10 ml, 50 ml of n-hexane was added, and the solution was cooled overnight to give 5.96 g of crystalline solid in the form of yellow needles. The solid was dissolved in 5 ml of tetrahydrofuran at room temperature and 7 ml of n-hexane was added. After cooling over the weekend, 4.220 g of large, pale yellow prisms of trans-chloro(triphenoxytin)bis(triethylphosphine)-platinum(II), trans-$[PtCl(P(C_2H_5)_3)_2Sn(OC_6H_5)_3]$, mp 92°–93°, was obtained. Nmr ($CD_2Cl_2$): 7.05 ppm (15H, aromatic), 2.25 ppm, multiplet and 1.15 ppm, quintet (30H, ethyl protons).

Anal. Calcd. for $C_{30}H_{45}O_3P_2ClSnPt$: C, 41.64; H, 5.24; P, 7.16; Sn, 13.72. Found: C, 41.88; H, 5.41; P, 7.14; Sn, 12.00.

The sodium triphenoxytin monotetrahydrofuranate used in this example was prepared by the following procedure. To a mixture of 2.84 g of dimethoxytin, 1.87 g of sodium phenoxide, and 3.03 g of phenol was added 30 ml of tetrahydrofuran. Solution occured and the solvent was removed under vacuum overnight. The solid product was dissolved in 25 ml of benzene, the solution was filtered, and 1 ml of THF was added to the filtrate. A total of 40 ml of hexane was added and 4.93 g of white, crystalline sodium triphenoxytin monotetrahydrofuranate $NaSn(OC_6H_5)_3 \cdot C_4H_8O$ was obtained, mp 122.5°–124°.

Anal. Calcd. for $C_{22}H_{23}O_4SnNa$: C, 53.6; H, 4.70; Sn, 24.05; Found: C, 53.75; H, 4.78; Sn, 22.67.

When sodium triphenoxytin monotetrahydrofuranate is replaced with tetraphenylarsonium triphenoxytin in the process, trans-chloro(triphenoxytin)bis(triethylphosphine)-platinum(II) is similarly obtained. The tetraphenylarsonium salt is prepared as follows: A solution of 4.188 g of tetraphenylarsonium chloride in 200 ml of acetone and 2.0 ml of ethanol was added to a solution of 4.930 g of sodium triphenoxytin monotetrahydrofuranate to give a fine white precipitate. The reaction mixture was filtered through diatomaceous earth, and the solvent was removed under vacuum to give a pale yellow residue. The residue was dissolved in 50 ml of tetrahydrofuran, filtered, and about 10 ml of n-hexane added. After cooling overnight, 5.525 g of crystalline tetraphenylarsonium triphenoxytin was obtained. Recrystallizing twice from tetrahydrofuran/n- hexane gave 3.405 g of off-white crystals, m.p. 135.5°–137°.

Nmr (DMSO$_{d_6}$/TMS): 7.8 ppm (20H, aromatic); 6.8 ppm (16H, aromatic).

Anal. Calcd. for $C_{42}H_{35}O_3SnAs$: C, 64.56; H, 4.51; Sn, 15.19; As, 9.59; Found: C, 71.14; H, 5.51; Sn, 5.64; As, 4.44.

EXAMPLE 2

To a clear, yellow solution of 2.513 g of transdichlorobis(triethylphosphine)platinum(II) in 10 ml of THF was added a solution of 2.702 g of sodium tribenzoatetin . ½ tetrahydrofuranate in 10 ml of THF. The resulting solution was stirred three hours at room temperature under nitrogen, filtered through diatomaceous earth, and the filtrate was concentrated under vacuum to give a flaky, white solid. The solid was dissolved in 5 ml of tetrahydrofuran, filtered, and 10 ml of n-hexane was added. After standing at room temperature overnight, a total of 2.230 g of white crystalline trans-chloro(tribenzoatetin)bis(triethylphosphine)platinum-(II), trans-[PtCl(P($C_2H_5$)$_3$)$_2$-Sn($O_2CC_6H_5$)$_3$], mp 141°, was obtained. Nmr(CDCl$_3$/TMS): 7.5 and 6.8 ppm (15 H, aromatic), 1.8 and 0.5 ppm (30 H, ethyl protons).

Anal. Calcd. for $C_{33}H_{45}O_6P_2ClSnPt$: C, 41.77; H. 4.78 P, 6.53; Sn, 12.51; Found: C, 41.37; H, 4.88; P, 6.70; Sn, 11.98.

The sodium tribenzoatetin . ½ tetrahydrofuranate used in this example was prepared by the following procedure. A mixture of 1.81 g of dimethoxytin, 1.44 g of sodium benzoate, and 2.44 g of benzoic acid in 15 ml of tetrahydrofuran was stirred overnight under nitrogen. The solvent was removed under vacuum from the solution and the solid residue was taken up in 20 ml of tetrahydrofuran and filtered. To the filtrate was added 40 ml of n-hexane and 3.080 g of sodium tribenzoatetin . ½ tetrahydrofuranate, NaSn($O_2CC_6H_5$)$_3$. ½ $C_4H_8O$, separated from solution, mp >240°. Nmr (DMSO): 7.95 and 7.45 ppm (15H, aromatic), 3.6 and 1.8 ppm (4.25H, multiplets, tetrahydrofuranate protons).

Anal. Calcd. for $C_{23}H_{19}O_{6.5}SnNa$: C, 51.11; H, 3.54; Sn, 21.96; Found: C, 51.45; H, 3.86; Sn, 21.36.

When sodium tribenzoatetin . ½ tetrahydrofuranate is replaced with tetrabutylammonium tribenzoatetin in the process, trans-chloro(tribenzoatetin)bis(triethylphosphine) platinum(II) is similarly obtained. The tetrabutylammonium salt is obtained by reaction of tetrabutylammonium bromide with sodium tribenzoatetin.½ tetrahydrofuranate in THF solution. The product is precipitated by addition of hexane, and it is obtained as a white, crystalline solid, m.p. 160°–163°.

Nmr (DMSO$_{d_6}$): 7.9 and 7.5 ppm (15H, aromatic); 3.6 and 1.6 ppm, multiplets, 1.0 ppm doublet, (36 H, n-butyl protons).

Anal. Calcd. for $C_{37}H_{51}O6NSn$: C, 61.34, H, 7.10; N, 1.93; Sn, 16.38. Found: C, 60.15; H, 7.01; N, 3.08; Sn, 13.93.

EXAMPLE 3

To a solution of 1.774 g of trans-dibromobis(triethylphosphine)platinum(II) in 10 ml of THF was added a solution of 1.480 g of sodium triphenoxytin monotetrahydrofuranate in 10 ml of THF to give a pale yellow suspension. The suspension was stirred at room temperature under nitrogen, filtered, and the filtrate evaporated to leave a yellow crystalline residue. The residue was dissolved in a minimum amount of tetrahydrofuran, the solution was filtered, and n-hexane was added to the filtrate. After cooling overnight, 1.155 g of pale yellow, crystalline trans-bromo(triphenoxytin)bis(triethylphosphine)platinum(II), trans-[PtBr(P($C_2H_5$)$_3$)$_2$Sn(O$C_6H_5$)$_3$] was obtained, mp 90°–91°. Nmr(CD$_2$Cl$_2$): 6.95 ppm (15H, aromatic), 2.25 and 1.0 ppm (30H, ethyl protons).

Anal. Calcd. for $C_{30}H_{45}O_3P_2BrSnPt$: C, 39.60; H, 4.99; P, 6.81; Sn, 13.05 Found: C, 39.47; H, 4.97; P, 6.85; Sn, 12.04.

EXAMPLE 4

To a solution of 2.513 g of trans-dichlorobis(triethylphosphine)platinum(II) in 10 ml of THF was added a solution of 4.934 g of sodium triphenoxytin monotetrahydrofuranate in 10 ml of THF to give a cloudy, orange solution. The solution was stirred for three hours at room temperature under nitrogen, and then filtered through diatomaceous earth. The filtrrate was concentrated under vacuum to a yellow-orange residue. The residue was dissolved in 35 ml of tetrahydrofuran, filtered, and 20 ml of n-hexane added. After standing overnight at room temperature, 2.139 g of bright yellow crystalline trans-bis(triphenoxytin)bis(triethylphosphine)-platinum(II), trans-[Pt(P($C_2H_5$)$_3$)$_2$(Sn(O$C_6H_5$)$_3$)$_2$] was obtained, mp 152°–153°.

Nmr(CDCl$_3$/TMS): 6.9 ppm (30H, aromatic), 2.6 and 0.9 ppm (30H, ethyl protons).

Anal. Calcd. for $C_{48}H_{60}O_6P_2Sn_2Pt$: C, 46.97; H, 4.93; Sn, 19.34; Found: C, 46.44; H, 5.02; Sn, 18.46.

EXAMPLE 5

To a solution of 0.827 g of trans-dichlorobis-(triethylphosphine)palladium(II) in 10 ml of THF was added a solution of 0.987 g of sodium triphenoxytin monotetrahydrofuranate in 10 ml of THF. The dark yellow suspension was stirred for five minutes at room temperature under nitrogen, the solution was filtered through diatomaceous earth, and the filtrate was concentrated under vacuum to a yellow oil. About 5 ml of tetrahydrofuran was added to the oil followed by about 25 ml of n-hexane. After cooling overnight, 1.01 g of crystalline trans-chloro(triphenoxytin)bis(triethylphosphine)-palladium(II), trans-[PdCl(P($C_2H_5$)$_3$)$_2$Sn(O$C_6H_5$)$_3$] was obtained as yellow needles, mp 94°–95°.

Nmr(CDCl$_3$/TMS): 6.98 ppm (15H, aromatic), 2.15 and 1.03 ppm (30 H, ethyl protons).

Anal. Calcd. for $C_{30}H_{45}O_3P_2ClSnPd$: C, 46.41; H, 5.84; P, 7.98; Sn, 15.29 Found: C, 46.20; H, 5.82; P, 7.74; Sn, 12.50.

EXAMPLE 6

Following essentially the procedure of Example 5, reaction of 0.827 g of trans-dichlorobis(triethylphosphine)-palladium(II) with 1.9736 g of sodium triphenoxytin monotetrahydrofuranate gave 0.689 g of yellow crystalline trans-bis(triphenoxytin(bis(triethylphosphine)palladium(II), trans-[Pd(P($C_2H_5$)$_3$)$_2$(Sn(O$C_6H_5$)$_3$)$_2$], mp 141°–142°.

Nmr (CDCl$_3$/TMS): 6.85 ppm (30 H, aromatic), 2.45 and 0.90 ppm (30 H, ethyl protons).

Anal. Calcd. for $C_{48}H_{60}O_6P_2Sn_2Pd$: C, 50.63; H, 5.31; P, 5.44; Sn, 20.85 Found: C, 48.64; H, 5.82; P, 5.71; Sn, 18.69.

EXAMPLE 7

Following essentially the procedure of Example 5, reaction of 0.827 g of trans-dichlorobis(triethylphosphine)-palladium(II) with 1.081 g of sodium tribenzoatetin . ½ tetrahydrofuranate gave 0.522 g of large, yellow prisms of trans-chloro(tribenzoatetin)bis(triethylphosphine)palladium(II), trans-[PdCl(P(C$_2$H$_5$)$_3$)$_2$Sn(O$_2$CC$_6$H$_5$)$_3$], mp 144°–146°.

Nmr (CDCl$_3$): 7.6 and 6.9 ppm (15H, aromatic), 1.7 and 0.6 ppm (35H, ethyl protons).

Anal. Calcd. for C$_{33}$H$_{45}$O$_6$ClP$_2$SnPd: C, 46.10; H, 5.27; Sn, 13.75. Found: C, 47.17; H, 5.37; Sn, 13.99.

EXAMPLE 8

To a clear, colorless solution of 1.775 g of dichlorobis(triphenylphosphite)platinum(II) in about 40 ml of THF was added a clear, colorless solution of 0.986 g of sodium triphenoxytin monotetrahydrofuranate in about 40 ml of THF. The resulting cloudy, orange solution was stirred overnight at room temperature under nitrogen, filtered through diatomaceous earth and the filtrate was concentrated to leave an orange solid. About 15 ml of tetrahydrofuran was added to the orange solid, the solution was filtered, and about 10 ml of n-hexane was added to the orange filtrate. Upon cooling overnight, 1.089 g of yellow, crystalline trans-chloro(triphenoxytin)bis(triphenylphosphite)platinum(II), trans-[PtCl(P(OC$_6$H$_5$)$_3$)$_2$Sn(OC$_6$H$_5$)$_3$] was obtained, mp 151°–152°, after recrystallization.

Anal. Calcd. for C$_{54}$H$_{45}$O$_9$ClP$_2$SnPt: C, 51.92; H, 3.63; P, 4.97; Sn, 9.51 Found: C, 51.98; H, 3.88; P, 4.85; Sn, 10.98.

EXAMPLE 9

Following essentially the procedure of Example 8, reaction of 1.775 g of dichlorobis(triphenylphosphite)-platinum(II) with 1.972 g of sodium triphenoxytin monotetrahydrofuranate gave after crystallization from benzene/n-hexane 1.147 g of yellow, crystalline trans-bis(triphenoxytin)bis-(triphenylphosphite)platinum-(II), trans-[Pt(P(OC$_6$H$_5$)$_3$)$_2$-(Sn(OC$_6$H$_5$)$_3$)$_2$], mp 177°–180°.

Nmr (CDCl$_3$/TMS): 7.18 ppm (30H singlet, aromatic), 6.6–7.3 ppm (30H, multiplets, aromatic).

Anal. Calcd. for C$_{72}$H$_{60}$O$_{12}$P$_2$Sn$_2$Pt: C, 53.65; H, 3.76; P, 3.84; Sn, 14.73. Found: C, 53.28; H, 3.85; P, 2.79; Sn, 14.33.

EXAMPLE 10

Following essentially the procedure of Example 8, reaction of 0.827 g of trans-dichlorobis(triethylphosphine)-palladium(II) with 2.40 g of sodium tris(p-fluorophenoxy)tin ditetrahydrofuranate gave after crystallization from benzene/n-hexane 0.263 g of granular, orange, crystalline trans-bis-(tris(p-fluorophenoxy)tin)bis(triethylphosphine)palladium(II),

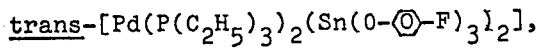

mp 176°–179°.

Anal. Calcd. for C$_{48}$H$_{54}$O$_6$F$_6$P$_2$Sn$_2$Pd: C, 46.24; H, 4.37; P, 4.97 Found: C, 45.34; H, 4.08; P, 4.45.

The sodium tris(p-fluorophenoxy)tin ditetrahydrofuranate used in this example was prepared by the following procedure. To a cloudy, colorless solution of 4.525 g of dimethoxytin and 3.350 g of sodium para-fluorophenoxide in tetrahydrofuran was added a solution of 5.605 g of p-fluorophenol in tetrahydrofuran (250 ml total volume). The solution was stirred for 3 hours at room temperature under nitrogen, filtered, and the solvent was removed under vacuum to leave a colorless solid. The solid was crystallized by dissolution in 2:1 by volume benzene:tetrahydrofuran and addition of 4 parts by volume of n-hexane. Total volume of crystallization solvents was about 300 ml. A yield of 4.031 g of clear prisms of sodium tris(p-fluorophenoxy)tin ditetrahydrofuranate,

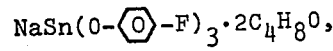

mp>230°, was obtained.

Nmr (DMSO/TMS): 6.7 ppm (12H, multiplets, aromatic), 3.6 and 1.75 ppm (14.7H, tetrahydrofuranate protons).

Anal. Calcd. for C$_{26}$H$_{28}$O$_5$F$_3$SnNa: C, 50.40; H, 4.56; F, 9.20; Sn, 19.13. Found: C, 50.30; H, 4.58; F, 8.85; Sn, 17.38.

EXAMPLE 11

To a solution of 1.75 g of trans-dichlorobis(tri-o-tolylphosphite)palladium(II) in THF was added a solution of 0.987 g of sodium triphenoxytin monotetrahydrofurane in 10 ml of THF to give a yellow-orange suspension. An additional 0.987 g of sodium triphenoxytin monotetrahydrofuranate in THF was added, and the suspension was stirred about four hours at room temperature under nitrogen. It was filtered through diatomaceous earth, and the solvent was removed under vacuum. The residue was crystallized from benzene-hexane to give 0.083 g of yellow, crystalline trans-bis(triphenoxytin)-bis(tri-o-tolylphosphite)-platinum(II),

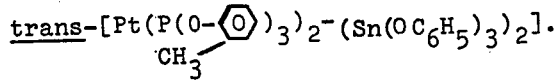

An additional 0.74 g of product was obtained by further concentration of the filtrate.

EXAMPLE 12

To a colorless solution of 0.935 g of trans-hydridochlorobis(triethylphosphine)platinum(II) in 10 ml of THF was added a solution of 0.986 g of sodium triphenoxytin monotetrahydrofuranate in 10 ml of THF. The orange solution was stirred for 30 minutes under nitrogen at room temperature and then filtered through diatomaceous earth. The filtrate was concentrated under vacuum to leave the product, trans-hydrido-(triphenoxytin)bis(triethylphosphine)platinum(II). trans-[PtH(P(C$_2$H$_5$)$_3$)$_2$Sn(OC$_6$H$_5$)$_3$], as a red-brown oil. The infrared spectrum of the product showed strong hydride absorption at 2100 cm$^{-1}$.

Nmr (C$_6$D$_6$/TMS): 6.6–7.5 ppm (15 H multiplets, aromatic), 0.8 and 1.75 ppm (30 H, C$_2$H$_5$), − 7.3 ppm (1 H, triplet, hydride).

EXAMPLE 13

To a solution of 1.75 g of trans-dichlorobis (tri-o-tolylphosphite)platinum(II) in 8 ml of THF was added a solution of 0.987 g of sodium triphenoxytin monotetrahydrofuranate in 8 ml of THF to give a bright yellow suspension. The reaction mixture was stirred at room temperature under nitrogen for 3 hours, filtered, and the solvent removed from the filtrate under vacuum. The residue solid was dissolved in 5 ml of benzene, filtered, and hexane added to give, after cooling overnight, 0.471 g of yellow-red, crystalline trans-chloro(triphenoxytin)bis(tri-o-tolylphosphite)platinum(II),

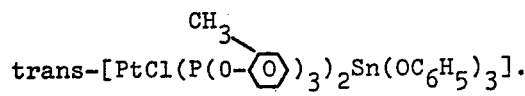

The slightly impure complex melted at 72°–76° and was active as a butadiene dimerization catalyst.

Nmr (CDCl$_3$): 6.0–7.5 ppm (39H, aromatic), 1.7–2.3 ppm (12H, doublet and multiplet).

Anal. Calcd. for C$_{60}$H$_{47}$O$_9$P$_2$SnClPt: C, 55.46; H, 3.58 Found: C, 50.94; H, 4.17.

EXAMPLE 14

To a solution of 0.950 g of trans-dichlorobis(triethylphosphine)platinum(II) in 10 ml of THF was added a solution of 0.926 g of sodium tris(p-methylphenoxy)tin in 10 ml of THF to give a cloudy, orange solution. The reaction mixture was stirred 4 hrs at room temperature under nitrogen, filtered through diatomaceous earth, and the solvent removed from the filtrate under vacuum to leave an orange oil. Efforts to crystallize the orange oil were unsuccessful. The oil was heated under vacuum which gave an orange solid which is largely trans-[chlorobis(triethylphosphine)[tris-(p-methylphenoxy)tin]platinum(II),

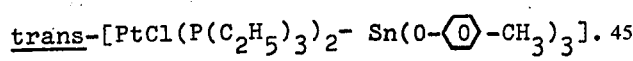

Nmr (CDCl$_3$): 6.88 ppm (10H, singlet, aromatic); 2.2 ppm (singlet), 1 ppm(quintet), and 1.9–2.5 ppm (multiplets) total of 39 H. The complex is active as a butadiene dimerization catalyst.

The sodium tris(p-methylphenoxy) tin used in this example was prepared by reaction of dimethoxytin (3.62 g), sodium p-methylphenoxide (2.6 g) and p-cresol (4.32 g) in THF (40 ml) at room temperature under nitrogen for 3 hours. The reaction mixture was filtered and the filtrate was concentrated under vacuum to leave the crude product as a white solid. The solid was crystallized from benzene (10 ml)/hexane (5 ml) to give 2.602 g of sodium tris(p-methylphenoxy)tin,

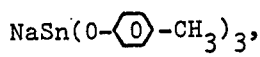

as white platelets, mp 93°–104°.

Anal. Calcd. for C$_{21}$H$_{21}$O$_3$SnNa: C, 54,55; H, 4.59; Sn, 25.62. Found: C, 50.00, H, 5.05; Sn, 26.92.

The starting materials of the formula MX$_2$L$_2$ are known compounds, as described for example, by J. Chatt et al., J. Chem. Soc. p. 5075 (1962); G. Booth, Advances in Inorganic Chemistry and Radiochemistry 6, 1 (1964); and K. A. Jensen, Z. anorg. allg. Chem. 229, 265 (1936).

Table 1 shows various examples of L groups, R′$_3$P and (R′O)$_3$P, which can be used to prepare suitable platinum and palladium starting materials.

TABLE 1

| R′$_3$P |
| --- |
| Triethylphosphine |
| Tri-n-butylphosphine |
| Dimethylphenylphosphine |
| Tri-n-propylphosphine |
| Tri-o-tolylphosphine |
| Methyldiphenylphosphine |
| Ethyldiphenylphosphine |
| Hexyldiphenylphosphine |
| Triphenylphosphine |
| Tri-p-tolylphosphine |
| Tri-m-tolylphosphine |
| Trimethylphosphine |
| Tri-p-ethylphenylphosphine |
| Triisopropylphosphine |
| Tri-sec-butylphosphine |
| Tri-2-methylbutylphosphine |
| Tripentylphosphine |
| Triisopentylphosphine |
| Trihexylphosphine |
| Dimethylethylphosphine |
| Methyldiethylphosphine |
| Ethyl-t-butylisopropylphosphine |
| Dipropylbutylphosphine |
| Dimethyl-p-butylphenylphosphine |
| Dimethyl-3,4-dimethylphenylphosphine |
| Diethyl-p-chlorophenylphosphine |
| Diethyl-p-bromophenylphosphine |
| Diethyl-o-tolylphosphine |
| Diethyl-m-tolylphosphine |
| Diethyl-p-ethylphenylphosphine |
| Diethyl-2-methyl-5-isopropylphenylphosphine |
| Diethyl-2,4,5-trimethylphenylphosphine |
| Diethyl-1-naphthylphosphine |
| Tri(α-naphthyl)phosphine |
| Tris(4-biphenylyl)phosphine |
| Diphenyl-2-chloro-4-methylphenylphosphine |
| Phenyldi(p-bromophenyl)phosphine |
| Phenyldi(4-methyl-1-naphthyl)phosphine |
| Tri(2-chloroethyl)phosphine |
| Tri(2-fluoroethyl)phosphine |
| Diisopropyl-p-tolylphosphine |
| Methyldi(p-tolyl)phosphine |
| (R′O)$_3$P |
| Trimethyl phosphite |
| Triphenyl phosphite |
| Tri(o-tolyl) phosphite |
| Tri(2,4-dimethylphenyl) phosphite |
| Tri(n-butyl) phosphite |
| Dimethyl phenyl phosphite |
| Diethyl phenyl phosphite |
| Methyl diphenyl phosphite |
| Ethyl diphenyl phosphite |
| Hexyl diphenyl phosphite |
| Triethyl phosphite |
| Triisopropyl phosphite |
| Tripentyl phosphite |
| Dipropyl butyl phosphite |
| Dimethyl-3,4-dimethylphenyl phosphite |
| Diethyl-p-chlorophenyl phosphite |
| Diethyl-p-bromophenyl phosphite |
| Diethyl-p-fluorophenyl phosphite |
| Diethyl-2,4,5-trimethylphenyl phosphite |
| Diethyl-1-naphthyl phosphite |
| Diethyl-2-naphthyl phosphite |
| Tri(α-naphthyl) phosphite |
| Diphenyl-2-chloro-4-methylphenyl phosphite |
| Phenyl di(4-methyl-1-naphthyl) phosphite |
| Tri(2-chloroethyl) phosphite |
| Tri(2-fluoroethyl) phosphite |
| Tri-n-propyl phosphite |

Additional compounds of the invention are shown in Table 2 made by reacting $MX_2L_2$ with $M'^+SnR_2^-$.

TABLE 2

| $MX_2L_2$ | $M'^+SnR_3^-$ | Product |
|---|---|---|
| $((n-C_4H_9)_3P)_2PtCl_2$ | $Na^+Sn(OC_6H_5)_3^-$ | $((n-C_4H_9)_3P)_2Pt(Cl)Sn(O_6H_5)_3$ |
| $((n-C_4H_9)_3P)_2PtCl_2$ | $Na^+Sn(OC_6H_5)_3^-$ | $((n-C_4H_9)_3P)_2Pt(Sn(OC_6H_5)_3)_2$ |
| $((C_5H_{11})_3P)_2PtBr_2$ | $K^+Sn(OC_6H_3Br_2-2,4)_3^-$ | $((C_5H_{11})_3P)_2Pt(Br)Sn(OC_6H_3Br_2-2,4)_3$ |
| $([(C_2H_5)_2(o-tolyl)]_3P)_2PtHBr$ | $Li^+Sn(O_2CC_6H_3(CH_3)_2-2,4)_3^-$ | $([(C_2H_5)_2(o-tolyl)]_3P)_2Pt(H)Sn(O_2CC_6H_3(CH_3)_2-2,4)_3$ |
| $((C_2H_5)_3P)_2PdCl_2$ | $Na^+Sn(O-1-naphthyl)_3^-$ | $((C_2H_5)_3P)_2Pd(Cl)Sn(O-1-naphthyl)_3$ |
| $((C_2H_5)_3P)_2PdCl_2$ | $Na^+Sn(O-1-naphthyl)_3^-$ | $((C_2H_3)_3P)_2Pd(Sn(O-1-naphthyl)_3)_2$ |
| $((C_6H_5)_3P)_2PdI_2$ | $Na^+Sn(O_2C-4-biphenylyl)_3^-$ | $((C_6H_5)_3P)_2Pd(Sn(O_2C-4-biphenyl)_3)_2$ |
| $((C_6H_5)_3P)_2PdI_2$ | $Na^+Sn(OC_6H_4(CH_3)-p)_3^-$ | $((C_6H_5)_3P)_2Pd(I)Sn(O-C_6H_4(CH_3)-p)_3$ |
| $((C_6H_5)_3P)_2PdBr_2$ | $Na^+Sn(OC_6H_4(C_3H_7)-p)_3^-$ | $((C_6H_5)_3P)_2Pd(Br)Sn(O-C_6H_4(C_3H_7-p)_3$ |
| $((C_6H_5)_3P)_2PdBr_2$ | $Na^+Sn(O_2CC_6H_3Cl_2-2,4)_3^-$ | $((C_6H_5)_3P)_2Pd(Br)Sn(O_2CC_6H_3Cl_2-2,4)_3$ |
| $((C_6H_5)_3P)_2PdBr_2$ | $K^+Sn(O_2CC_6H_4I-p)_3^-$ | $((C_6H_5)_3P)_2Pd(Br)Sn(O_2CC_6H_4I-p)_3$ |
| $((C_6H_5)_3P)_2PdBr_2$ | $Na^+Sn(OC_6H_4(C_2H_5)-o)_3^-$ | $((C_6H_5)_3P)_2Pd(Br)Sn(OC_6H_4(C_2H_5)-o)_3$ |
| $((C_2H_5O)_3P)_2PtCl_2$ | $Na^+Sn(OC_6H_2(CH_3)_3-2,4,5)_3^-$ | $((C_2H_5O)_3P)_2Pt(Cl)Sn(OC_6H_2(CH_3)_3-2,4,5)_3$ |
| $((C_2H_5O)_3P)_2PtCl_2$ | $Na^+Sn(OC_6H_4Cl-p)_3^-$ | $((C_2H_5O)_3P)_2Pt(Sn(Oc_6H_4Cl-p)_3)_2$ |
| $((C_2H_5O)_3P)_2PtCl_2$ | $K^+Sn(O_2CC_6H_3(i-C_3H_7)-2,4)_3^-$ | $((C_2H_5O)_3P)_2Pt(Cl)Sn(O_2CC_6H_3(i-C_3H_7)-2,4)_3$ |

The compounds of this invention are all useful as catalysts for the dimerization of butadiene. As described in Example A below, a number of dimers of butadiene may be obtained including 1,3,7-octatriene, 4-vinylcyclohexene, and 1,2-divinylcyclobutane. The dimers are useful as monomers in polymerization processes or in copolymerization with other monomers. The octadiene is employed as the diene or as the dienophile in Diels-Alder condensations. The butadiene dimers may be epoxidized to form epoxide products from which are formed useful epoxy resins through reaction with a variety of conventional curing agents. The ethylenic linkage(s) are hydrated or hydroxylated to form alcohols from which ethers, carboxylic esters, sulfates, sulfonates or the like are produced, or are halogenated to form halo derivatives useful, for example, as precursors for quaternary ammonium salts. Additionally, the dimers may be partially hydrogenated to form other olefinic products.

EXAMPLE A

An 80 ml Hastelloy C (Union Carbide Corporation) shaker tube was charged with 25 ml of benzene and 0.1 g of trans- hydrido(triphenoxytin)bis(triethylphosphine)platinum(II), the product of Example 12. The tube was cooled and 10 g of butadiene was added. The tube was heated at 150°C for 3 hours with shaking, cooled, and the reaction product was analyzed by gas chromatography on a ⅛in. × 12ft. column of 3% silicone (50% phenyl, methyl) on Gas Chrom Q. The sample was injected at a column temperature of 42°, and after 6 minutes the column was heated to 190° at a rate of 60°/min. Helium flow rate was 50 ml/min. In addition to recovered butadiene, the following products were obtained (area percentage amount shown).

Benzene, 78.9; 1,2-divinylcyclobutane, 1.3; 1,3,7-octatriene, 0.9; 4-vinylcyclohexene, 17.6; 1,5-cyclooctadiene, 0.5; miscellaneous trimers, 0.7.

When the compounds of Column I in Table 3 below were similarly employed as butadiene dimerization catalysts using the same procedure as described, the area percentage amounts (in the chromatograph column) of products shown in Column II were obtained.

TABLE 3

| Column I | Column II |
|---|---|
| trans-$[Pd(P(C_2H_5)_3)_2(Sn(OC_6H_5)_3)_2]$ | benzene, not calculated<br>1,2-divinylcyclobutane, small<br>1,3,7-octatriene, 3.1<br>4-vinylcyclohexene, 12.6<br>1,5-cyclooctadiene, 0.32 |
| trans-$[PtCl(P(C_2H_5)_3)_2Sn(O_2CC_6H_5)_3]$ | benzene, not calculated<br>1,2-divinylcyclobutane, not calculated<br>4-vinylcyclohexene, 24.5<br>1,5-cyclooctadiene, 0.8 |
| trans-$[Pd(P(C_2H_5)_3)_2(Sn(O$  $F)_3)_2]$ | benzene, 79<br>1,2-divinylcyclobutane, 1.4<br>1,3,7-octatriene, 0.2<br>4-vinylcyclohexene, 18.3<br>1,5-cyclooctadiene, 0.5<br>miscellaneous trimers, 0.6 |

We claim:
1. A trans compound of the formula

$$MX_{2-n}L_2(SnR_3)_n$$

wherein
  M is platinum or palladium;
  X is H, Cl, Br or I;
  L is $R'_3P$ or $(R'O)_3P$ in which
    R', alike or different, is aryl of 6–12 carbons, alkyl of 1–6 carbons and such groups containing up to two halogens;
  R, alike or different, is aryloxy of 6–12 carbons, arylcarboxy of 7–13 carbons and such groups containing up to two halogens; and
  n is 1 or 2.

2. A compound of claim 1 where M is platinum.
3. A compound of claim 1 where M is palladium.
4. A compound of claim 1 where $n = 1$.
5. A compound of claim 1 where $n = 2$.
6. A compound of claim 1 where R' is alkyl, phenyl or alkyl-substituted phenyl.

7. A compound of claim 1 where R is phenoxy or phenylcarboxy and such groups containing up to two alkyl groups of 1–6 carbons or up to two halogens.

8. The compound of claim 1 which has the formula trans-$[PtCl(P(C_2H_5)_3)_2Sn(OC_6H_5)_3]$.

9. The compound of claim 1 which has the formula trans-$[PtCl(P(C_2H_5)_3)_2Sn(O_2CC_6H_5)_3]$.

10. The compound of claim 1 which has the formula trans-$[PdCl(P(C_2H_5)_3)_2Sn(OC_6H_5)_3]$.

11. The compound of claim 1 which has the formula trans-$[PdCl(P(C_2H_5)_3)_2Sn(O_2CC_6H_5)_3]$.

12. The compound of claim 1 which has the formula trans-$[Pt(P(C_2H_5)_3)_2(Sn(OC_6H_5)_3)_2]$.

* * * * *

UNITED STATES PATENT OFFICE
CERTIFICATE OF CORRECTION

PATENT NO. : 3,975,415
DATED : August 17, 1976
INVENTOR(S) : Dale Robert Coulson and Linda P. Seiwell It is certified that error appears in the above-identified patent and that said Letters Patent are hereby corrected as shown below:

Abstract, line 3, "in" should be --is--.

Column 1, line 52, "SNR$_3$" should be --SNR$_3^-$--.

Column 3, line 55, "C$_{37}$H$_{51}$O6NSn" should be --C$_{37}$H$_{51}$O$_6$NSn--.

Column 4, line 19, "filtrrate" should be --filtrate--.

Column 6, line 28, "palladium" should be --platinum--.

Column 6, line 30, "drofurane" should be --drofuranate--.

Column 6, line 62, "." should be --,--.

Column 7, line 61, "(5" should be --(50 --.

Column 9, line 2, "SnR$_2$" should be --SnR$_3$--.

Column 10, Table 3 col. 1 last item, "(O    F)" should be --  --.

UNITED STATES PATENT OFFICE
CERTIFICATE OF CORRECTION

Patent No. 3,975,415  Dated August 17, 1976

Inventor(s) Dale Robert Coulson and Linda P. Seiwell

It is certified that error appears in the above-identified patent and that said Letters Patent are hereby corrected as shown below:

Column 11, line 5, "$(C_2 551)_3$" should read -- $(C_2H_5)_3$ --.

Signed and Sealed this

Eighteenth Day of October 1977

[SEAL]

Attest:

RUTH C. MASON
*Attesting Officer*

LUTRELLE F. PARKER
*Acting Commissioner of Patents and Trademarks*